US007183374B2

(12) United States Patent
Brenner et al.

(10) Patent No.: US 7,183,374 B2
(45) Date of Patent: Feb. 27, 2007

(54) METHOD OF REMOVING TRANSITION METALS

(75) Inventors: Michael Brenner, Bingen (DE); Siegfried Meineck, Ingelheim (DE); Thomas Wirth, Stadecken-Elsheim (DE)

(73) Assignee: Boehringer Ingelheim International GmbH, Ingelheim (DE)

( * ) Notice: Subject to any disclaimer, the term of this patent is extended or adjusted under 35 U.S.C. 154(b) by 267 days.

(21) Appl. No.: 10/991,981

(22) Filed: Nov. 18, 2004

(65) Prior Publication Data

US 2005/0119453 A1    Jun. 2, 2005

Related U.S. Application Data

(60) Provisional application No. 60/528,747, filed on Dec. 11, 2003.

(30) Foreign Application Priority Data

Nov. 20, 2003   (EP)   ................... 03026689

(51) Int. Cl.
*C07K 5/12*   (2006.01)
*C07D 487/14*   (2006.01)
*C07F 15/00*   (2006.01)

(52) U.S. Cl. .................. 530/317; 530/344; 540/460; 548/101; 556/21; 556/22

(58) Field of Classification Search ............. 530/317, 530/344; 540/460; 548/101; 556/21, 22
See application file for complete search history.

(56) References Cited

U.S. PATENT DOCUMENTS

| 6,376,690 B1 | 4/2002 | Grubbs et al. |
| 2005/0154186 A1* | 7/2005 | Gallou et al. ............... 530/317 |
| 2005/0215423 A1 | 9/2005 | Brenner et al. |

FOREIGN PATENT DOCUMENTS

| WO | WO 00/59929 | 10/2000 |
| WO | WO 03/053349 A2 | 7/2003 |
| WO | WO 03/064455 A2 | 8/2003 |
| WO | WO 03/066103 A1 | 8/2003 |
| WO | WO 2004/030670 A1 | 4/2004 |

OTHER PUBLICATIONS

Cho Jong Hyun and B. Moon Kim: An Efficient Method for Removal of Ruthenium Byproducts from Olefin Metathesis Reactions; Organic Letters; vol. 5, No. 4; 2003; pp. 531-533.
Tina M. Trnka, et al; Ruthenium Alkylidene Complexes Coordinated with Tricyclohexyiphosphine and Heterocyclic N-donor Ligands; ARKIVOC; vol. xiii; 2002; pp. 28-41.
Yu Mi Ahn, et al; A Convenient Method for the Efficient Removal of Ruthenium Byproducts Generated during Olefin Metathesis Reactions; Organic Letters; vol. 3, No. 9; 2001; pp. 1411-1413.
C. W. Bielawski, et al; Highly Efficient Syntheses of Acetoxy- and Hydroxy-Terminated Telechelic Poly (Butadiene)s using Ruthenium Catalysts Containing N-heterocyclic Ligands; Polymer, vol. 42, No. 11; 2001; pp. 4939-4945.
Leo A. Paquette et al; A Convenient Method for Removing All Highly-Colored Byproducts Generated during Olefin Metathesis Reactions; Organic Letters; vol. 2, No. 9; 2000: pp. 1259-1261.
Heather D. Maynard and Robert H. Grubbs; Purification Technique for the Removal of Ruthenium from Olefin Metathesis Reaction Products; Tetrahedron Letters; vol. 40, No. 22; 1999; pp. 4137-4140.
Montse Llinas-Brunet, et al; Structure-Activity Study on a Novel Series of Macrocyclic Inhibitors of the Hepatitis C Virus NS3 Protease Leading to the Discovery of BILN 2061; Journal of Medicinal Chemistry; vol. 47, No. 7; 2004; pp. 1605-1608.
Daniel Lamarre, et al; An NS3 Protease Inhibitor with Antiviral Effects in Humans Infected with Hepatitis C Virus; Letters to Nature; vol. 426, No. 6963; 2003; pp. 186-189.
Youla S. Tsantrizos, et al; Macrocyclic Inhibitors of the NS3 Protease as Potential Therapeutic Agents of Hepatitis C Virus Infection; Angewandte Chemie, International Edition; vol. 42, No. 12; 2003; pp. 1356-1360.

* cited by examiner

*Primary Examiner*—Porfirio Nazario-Gonzalez
(74) *Attorney, Agent, or Firm*—Michael P. Morris; Mary-Ellen M. Devlin; Philip I. Datlow

(57) ABSTRACT

A process for diminishing the concentration of a metal complex from a solution containing said complex by the addition of an optionally fused and/or optionally substituted heterocyclic compound. The added compound is a solubility-enhancing compound that enhances the solubility of said complex in a second solution. Thereafter the solution containing said complex can be extracted with the second solution.

23 Claims, No Drawings

METHOD OF REMOVING TRANSITION METALS

RELATED APPLICATIONS

Benefit of U.S. Provisional Application Ser. No. 60/528,747, filed on Dec. 11, 2003 is hereby claimed.

BACKGROUND OF THE INVENTION

1. Technical Field

This invention relates to a method of diminishing the concentration of a metal complex from a solution containing said complex by the addition of an optionally fused and/or optionally substituted heterocyclic compound. The added compound is a solubility-enhancing compound that enhances the solubility of said complex in a second solution. Thereafter the solution containing said complex can be extracted with the second solution.

2. Background Information

Despite the ubiquitous use of metal complexes in organic reactions, a simple method for their removal has yet to be discovered. Unfortunately, residual metals often must be removed from the reaction mixture because they can interfere with subsequent transformations and can pose problems for shelf-life and use of the final product.

Current methods for removing metal complexes involve running the reactant mixture through numerous columns or other similarly rigorous purification strategies. In addition to being cumbersome, these procedures are time consuming and labour intensive. As uses for metal complexes increases, a simple and facile method for their removal is increasingly needed and desired.

U.S. Pat. No. 6,376,690 discloses a method of removing residual metals from a solution by adding a solubility-enhancing compound, wherethrough the relative solubilities between two solutions are manipulated so as to cause the metal complex in a first solution to transfer into a second solution that is generally immiscible with the first solution. The removal of the second solution thus also removes the metal complex from the reaction mixture.

U.S. Pat. No. 6,376,690 recommend phosphines as useful solubility-enhancing compounds. However, the examples disclosed in this invention, only demonstrate that the use of a special water-soluble phosphine, i.e. trishydroxymethylphosphine (THP) in combination with triethylamine, is able to reduce the Ruthenium content of different simple ether and ester products. With respect to the large scale synthesis of more highly functionalized organic compounds, treatments with THP solutions may cause undesired side reactions. These side reactions may be due to formaldehyde present in THP solutions, which are most easily accessible for large scale operations by means of alkaline deformylation of commercially available aqueous tetrakis(hydroxymethyl)phosphonium salts (TKC).

Moreover, in view of a potential commercial use on large scale, phosphines generally exhibit the disadvantage of being very susceptible towards oxidation. This implies that special measures have to be taken to protect these air sensitive and/or pyrogenic compounds from contact to oxygen and therefore guarantee their desired efficiency. Hence, these phosphoric compounds are released in situ in separate vessels under inert conditions, increasing the complexity of the large scale processes. In addition, phosphines are toxic and therefore not useful in food or pharmaceutical industry, since any product contamination by these compounds has to be strictly avoided.

Surprisingly it was found, that these pitfalls can be avoided by the use of certain heterocyclic compounds with at least two nitrogen atoms as solubility enhancing compounds.

BRIEF SUMMARY OF THE INVENTION

This invention relates to a process for diminishing the concentration of a metal complex from a solution containing said complex by the addition of an optionally fused and/or optionally substituted heterocyclic compound. This compound is a solubility-enhancing compound that enhances the solubility of said complex in a second solution. Thereafter the solution containing said complex can be extracted with the second solution. In one embodiment of the invention, the relative solubilities between two solutions are manipulated so as to cause a metal complex in a first solution (typically the reaction mixture) to transfer into a second solution that is generally immiscible with the first solution. The removal of the second solution thus also removes the metal complex from the reaction mixture. This embodiment is particularly useful for separating the metal complex from the reaction product.

DETAILED DESCRIPTION OF THE INVENTION

The present invention generally relates to the discovery that the solubility of metal complexes may be readily manipulated by the addition of one or more solubility-enhancing compounds. This manipulation of the solubilities allows for the preparation of suitable samples for precise quantitative analysis and for the facile purification of the desired products from the reaction mixture containing one or more metal complexes.

In the most general sense, the present invention relates to a method of enhancing the solubility of a metal complex (or a combination of metal complexes) in a solution by the addition of one or more solubility-enhancing compounds to the solution.

Used Terms and Definitions

Terms not specifically defined herein should be given the meanings that would be given to them by one of skill in the art in light of the disclosure and the context. As used in the specification, however, unless specified to the contrary, the following terms have the meaning indicated and the following conventions are adhered to.

In the groups, radicals, or moieties defined below, the number of carbon atoms is often specified preceding the group, i.e. —$C_{1-6}$ alkyl means an alkyl group or radical having 1 to 6 carbon atoms. Unless otherwise specified below, conventional definitions of terms control and conventional stable atom valences are presumed and achieved in all formulas and groups.

The term "optionally substituted" as used herein, means that any one or more hydrogens on the designated atom is replaced with a selection from the indicated group, provided that the designated atom's normal valence is not exceeded, and that the substitution results in a stable compound.

The term "optionally fused" as used herein, means that two adjacent hydrogens on the designated ring are replaced with two atoms of another ring, provided that the designated atom's normal valence is not exceeded, and that the substitution results in a stable compound. Examples for fused rings are benzimidazole, purine or chinazoline.

The term "—C$_{1-6}$-alkyl" as used herein, either alone or in combination with another substituent, means acyclic, straight or branched chain alkyl substituents containing from one to six carbon atoms. The term —C$_{1-6}$-alkyl can include e.g. methyl, ethyl, propyl, butyl, hexyl, 1-methylethyl, 1-methylpropyl, 2-methylpropyl or 1,1-dimethylethyl.

The term "—C$_{1-6}$-alkoxy" as used herein, either alone or in combination with another substituent, means the substituent —O—C$_{1-6}$-alkyl wherein alkyl is as defined above containing up to six carbon atoms. Alkoxy includes methoxy, ethoxy, propoxy, 1-methyl-ethoxy, butoxy or 1,1-dimethylethoxy.

The term "—C$_{3-8}$-cycloalkyl" as used herein, either alone or in combination with another substituent, means a cycloalkyl substituent containing from three to six carbon atoms and includes cyclopropyl, cyclobutyl, cyclopentyl, cyclohexyl, cycloheptyl or cyclooctyl.

The term "—C$_{5-10}$-alkenylene" as used herein means a divalent alkenyl substituent derived by the removal of one or two hydrogen atom from each end of a unsaturated straight or branched chain aliphatic hydrocarbon containing from five to ten carbon atoms and at least one, two or three double bonds and includes, for example, —CH$_2$—CH$_2$—CH$_2$—CH=CH—, —CH$_2$—CH$_2$—CH=CH—CH$_2$—, —CH$_2$—CH$_2$—CH$_2$—CH$_2$—CH=.

The term "—C$_{5-10}$-alkynylene" as used herein means a divalent alkynyl substituent derived by the removal of one, two or three hydrogen atom from each end of a unsaturated straight or branched chain aliphatic hydrocarbon containing from five to ten carbon atoms and at least one or two triple bonds and includes, for example, —CH$_2$—CH$_2$—CH$_2$—C≡C—, —CH$_2$—CH$_2$—C≡C—CH$_2$—, —CH$_2$—CH$_2$—CH$_2$—CH$_2$—C≡.

The term "aryl" as used herein, either alone or in combination with another substituent, means either an aromatic monocyclic system or aromatic multicyclic systems containing carbon atoms. For example, aryl includes a phenyl or a naphthyl ring system.

The term "het" as used herein, either alone or in combination with another substituent, means a saturated or unsaturated heterocycle containing carbon atoms and one, two, three or four heteroatoms selected from nitrogen, oxygen and sulphur. Examples of suitable heterocycles include: tetrahydrofuran, thiophene, diazepine, isoxazole, piperidine, dioxane, morpholine, piperazine or

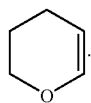

Although generally covered under the term "het", the term "heteroaryl" as used herein precisely defines an unsaturated heterocycle for which the double bonds form an aromatic system. Suitable example of heteroaromatic systems include: pyrimidine,

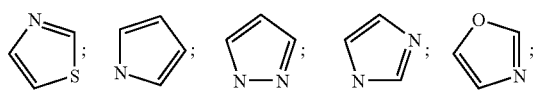

-continued

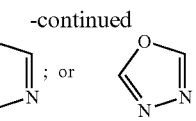

As used herein, the term "metal complexes" include the metal itself (e.g. Cu, Mg, Ru, Os, etc), its ions, and metal containing or metal associated compounds (either through covalent bounds or through other intermolecular forces such as chelation). Illustrative examples of metal complexes whose solubility's may be manipulated through the practice of the present invention include but are not limited to complexes of: cadmium, chromium, cobalt, copper, gold, iridium, iron, magnesium, manganese, mercury, molybdenum, nickel, osmium, palladium, platinum, rhenium, rhodium, ruthenium, silver, technetium, tungsten, and zinc.

As used herein, "solubility-enhancing compounds" are compounds that interact with a metal or transition metal complex in a manner that enhances the solubility of the metal moiety in the desired solution. Suitable examples of solubility-enhancing compounds are imidazole, pyrazole, triazole, pyridazine, pyrimidine, pyrazine, triazine, diazepine, triazepine, dihydro-imidazole, dihydro-pyrazole, tetrahydro-pyridazine, tetrahydro-pyrimidine, tetrahydro-pyrazine, dihydro-pyridazine, dihydro-pyrimidine, dihydro-pyrazine, tetrahydro-triazine, dihydro-triazine, tetrahydro-diazepine, dihydro-diazepine, tetrahydro-triazepine, dihydro-triazepine.

As used herein "adsorbent" are solid compounds that adsorb a metal or transition metal complex. So, if added to a solution containing impurities of a metal or a transition metal the concentration of said metal or transition metal is diminished in the liquid phase. Suitable examples for adsorbent are silica gel, charcoal, aluminium oxide or functionalized resins.

As used herein the term "protecting group" includes functional groups used for the protection of a hydroxy function. To protect the hydroxy function the protective group replaces the hydrogen atom of the hydroxy group, to unprotect the hydroxy group cleavage of the group-oxygen bond under reformation of the —OH group under mild conditions is possible.

As used herein the term "suitable leaving group" includes functional groups that are replaces the hydrogen atom of a hydroxy group. Then the group is displaced as stable species taking with it the bonding electrons. Typically the leaving group leaves as an anion taking the oxygen of the former hydroxy group with it. The better the leaving group, the more likely it is to depart.

A leaving group can be the same then a protecting group depending on the reaction to despatch the group. Examples of suitable leaving groups or protecting groups are 2.4.6-trimethylbenzoate, 2.4-dinitrophenyl, 2.4-dinitrophenylsulfenate, 2-chlorobenzoate, 2-trifluoromethylbenzyl, 2-trimethylsilylethyl, 3.4-dimethoxybenzyl, 3.4-dimethoxybenzyl, 3-phenylpropionate, 4-bromobenzoate, 4-nitrobenzoate, 9-anthryl, 9-fluorenylmethyl, □-naphthoate, acetate, allyl, allylsulfonate, benzoylformate, benzyl, benzyloxymethyl, benzylsulfonate, brosylate, chloroacetate, chlorodiphenylacetate, dichloroacetate, diethylisopropylsilyl, dimethylisopropylsilyl, diphenylacetate, diphenylmethyl, ethyl, isobutyl, isobutyrate, menthoxymethyl, methanesulfonate, methoxyacetate, methoxymethyl, methyl, monosuccinoate, nitrobenzyl, nitrophenyl, N-phenylcarbamate, p-acylaminobenzyl, p-chlorophenyl, p-cyanobenzyl, p-halobenzyl, phenoxyacetate, phenylacetate, p-methoxybenzyl, p-methoxyphenyl, p-phenylbenzoate, propargyl, t-butyl, tosylate, tribenzylsilyl, trichloroacetate, triethylsilyl, trifluoroacetate, triisopropylsilyl, trimethylsilyl, triphenylmethyl, triphenylsilyl, tris(trimethylsilyl)silyl, vinyl.

PREFERRED EMBODIMENTS

Preferred is a process for diminishing the concentration of a metal complex from a solution containing said complex by the addition of an optionally fused and/or optionally substituted het or hetaryl, wherein
  het is a four to eight membered, non-aromatic heterocyclic compound containing two, three or four nitrogen atoms and
  hetaryl is a five or six membered, aromatic heterocyclic compound containing two or three nitrogen atoms.

More preferred is a process for diminishing the concentration of a transition metal complex from a solution containing said complex by the addition of an optionally fused and/or optionally substituted het or hetaryl, wherein
  het is a four to eight membered, non-aromatic heterocyclic compound containing two, three or four nitrogen atoms and
  hetaryl is a five or six membered, aromatic heterocyclic compound containing two or three nitrogen atoms.

Most preferred is a process for diminishing the concentration of a transition metal complex from a solution containing said complex by the addition of an optionally fused het or hetaryl, wherein
  het is a four to eight membered, non-aromatic heterocyclic compound containing two, three or four nitrogen atoms, wherein each atom of the ring each independently is optionally substituted by —$C_{1-6}$-alkyl, —$C_{1-6}$-alkyl-OH, —$C_{1-6}$-alkoxy, —$C_{1-6}$-phenyl or phenyl and
  hetaryl is a five or six membered, aromatic heterocyclic compound containing two or three nitrogen atoms, wherein each atom of the ring each independently is optionally substituted by —$C_{1-6}$-alkyl, —$C_{1-6}$-alkyl-OH, —$C_{1-6}$-alkoxy, —$C_{1-6}$-phenyl or phenyl.

Another embodiment of the invention is a method of diminishing the concentration of a transition metal complex from a first solution containing said complex by the addition of a second solution, comprising the steps:
  adding a solubility-enhancing compound that enhances the solubility of said complex in the second solution;
  combining the first solution with the second solution wherein the second solution is immiscible with the first solution;
  mixing the first solution and second solution together; and,
  removing the second solution from the first solution;

wherein the solubility-enhancing compound is an optionally fused, heterocyclic compound containing at least 2 nitrogen atoms.

Preferred is a process, wherein the solubility-enhancing compound is an optionally fused five-, six- or seven membered aromatic or non-aromatic heterocyclic compound, containing two or three nitrogen atoms, wherein each atom of the ring each independently are optionally substituted by —$C_{1-6}$-alkyl, —$C_{1-6}$-alkyl-OH, —$C_{1-6}$-alkoxy, —$C_{1-6}$-phenyl or phenyl.

More preferred is a process, wherein the solubility-enhancing compound is selected from the group consisting of imidazole, benzimidazole, pyrazole or triazole.

Preferred is the process wherein the removed transition metal is selected from a group consisting of Cu, Ru, Os, Cd, Cr, Co, Ag, Ir, Fe, Mn, Hg, Mo, Ni, Pd, Pt, Re, Rh, Ag, Te, W or Zn.

More preferred is the process wherein the removed transition metal is selected from a group consisting of Cu, Ru, Fe, Ni, Pd, Pt, Rh or W, preferably Ru, Pd or Rh, particular preferred is Ru.

Most preferred is a process for diminishing the concentration of a Ru, Rh or Pd complex from a first solution containing said complex, comprising the steps:
  adding a solubility-enhancing compound that enhances the solubility of said complex in an aqueous solution;
  combining the first solution with an aqueous solution wherein the aqueous solution is immiscible with the first solution;
  mixing the first solution and the aqueous solution together; and,
  removing the aqueous solution from the first solution;

wherein the solubility-enhancing compound is selected from the group consisting of imidazole, benzimidazole, pyrazole or triazole.

In a preferred variation of the above method, an adsorbent is added after removing of the second solution. The method comprises the steps
  adding an adsorbent, preferably charcoal powder to the first solution;
  removing all solid residues from the first solution.

Therefore preferred is a process for diminishing the concentration of a Ru, Rh or Pd complex from a first solution containing said complex, comprising the steps:
  adding a solubility-enhancing compound that enhances the solubility of said complex in an aqueous solution; optionally ad an adsorbent;
  combining the first solution with an aqueous solution wherein the aqueous solution is immiscible with the first solution;
  mixing the first solution and the aqueous solution together; and,
  removing the aqueous solution from the first solution;
  adding charcoal powder to the first solution;
  removing all solid residues from the first solution wherein the solubility-enhancing compound is selected from the group consisting of imidazole, benzimidazole, pyrazole or triazole.

Another embodiment of the invention is a process for diminishing the concentration of a transition metal complex from a reaction mixture containing said complex, comprising:
  a) adding a heterocyclic compound containing at least 2 nitrogen atoms as a solubility-enhancing compound that enhances the solubility of said complex in the second solution;
  b) heating the first solution to 40–120° C.;
  c) stirring the resulting mixture for 20–720 minutes;
  d) extracting the first solution with an aqueous second solution.

Preferred is a process wherein the molar ratio between the transition metal and the solubility enhancing compound is from 1:10 to 1:600, preferably from 1:10 to 1:300, more preferably from 1:25 to 1:100, most preferably about 1:50.

Preferred is a process wherein step b) comprises, heating the first solution to 60–100° C., preferably 70–90° C., more preferably 75–85° C.

Preferred is a process wherein step a) comprises, adding an optionally fused five-, six- or seven membered aromatic or non-aromatic heterocyclic compound, containing two or three nitrogen atoms, wherein each atom of the ring each independently are optionally substituted by —$C_{1-6}$-alkyl, —$C_{1-6}$-alkyl-OH, —$C_{1-6}$-alkoxy, —$C_{1-6}$-phenyl or phenyl, preferably selected from the group consisting of imidazole, benzimidazole, pyrazole or triazole as a solubility-enhancing compound that enhances the solubility of said complex in the second solution.

Preferred is a process wherein step c) comprises, stirring the resulting mixture for 60–600 minutes, preferably 180–480 minutes, more preferably 300–420 minutes, most preferably 320–340 minutes.

Preferred is a process wherein step d) comprises the steps:
  extracting the first solution with hydrochloric acid, preferably 0.1–5.0 N HCl, more preferably 0.5–2.0 N HCl, most preferably 0.75–1.25 N hydrochloric acid; and thereafter
  extracting the first solution once, twice, thrice or more with water.

Therefore preferred is a process for diminishing the concentration of a Ru, Rh or Pd complex from a reaction mixture containing said complex, comprising the steps:
  a) adding a compound selected from the group consisting of imidazole, benzimidazole, pyrazole, triazole as a solubility-enhancing compound that enhances the solubility of said complex in the second solution;
  b) heating the first solution to 80° C.;
  c) stirring the resulting mixture for 120 minutes;
  d) extracting the first solution with 1N hydrochloric acid; and thereafter, extracting the first solution twice with water.

Also preferred is a process, wherein the remaining concentration of transition metal after steps a-d is same or less then 1000 ppm, <900 ppm, <800 ppm, preferably <700 ppm, <600 ppm, <500 ppm, in particular <400 ppm, <300 ppm, <200 ppm, <100 ppm, <50 ppm, <10 ppm or <5 ppm.

Preferred is also a variation of the process, wherein steps a) and b) are exchanged.

Preferred is a process wherein step d) is followed by the steps e-h comprising the steps,
  e) adding a solid adsorbent;
  f) heating the mixture to 20–100° C.
  g) stirring the resulting mixture for 10–500 minutes;
  h) removing the solid residues.

Preferred is a process wherein the solid adsorbent is charcoal powder.

Preferred is a process wherein step f) comprises, heating the first solution to 30–80° C., preferably 35–70° C., more preferably 40–60° C., most preferably 45–55° C.

Preferred is a process wherein step g) comprises, stirring the resulting mixture for 20–200 minutes, preferably 60–180 minutes, more preferably 100–140 minutes, most preferably 110–130 minutes.

Therefore preferred is a process for diminishing the concentration of a Ru, Rh or Pd complex from a reaction mixture containing said complex, comprising the steps:
  a) adding a compound selected from the group consisting of imidazole, benzimidazole, pyrazole, triazole as a solubility-enhancing compound that enhances the solubility of said complex in the second solution;
  b) heating the first solution to 80° C.;
  c) stirring the resulting mixture for 120 minutes;
  d) extracting the first solution with 1N hydrochloric acid; and thereafter, extracting the first solution twice with water;
  e) adding charcoal powder;
  f) heating the mixture to 50° C.
  g) stirring the resulting mixture for 120 minutes;
  h) filtering the solid residues off.

Also preferred is a process, wherein the remaining concentration of transition metal after steps a-h is same or less then 500 ppm, <400 ppm, preferably <300 ppm, <200 ppm, in particular <100 ppm, <50 ppm, <10 ppm or <5 ppm.

Also preferred is a process, wherein the first solution is the crude product solution of a metathesis reaction containing a compound of general formula 3,

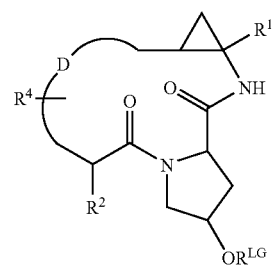

3 wherein
  $R^1$ is H, —$COR^3$, —$COOR^3$, —CO—$NHR^3$, —NH—$COR^3$, —NH—$COOR^3$;
  $R^2$ is —$OR^3$, —$NHR^3$, —NH—$COR^3$, —NH—$CONHR^3$, —NH—$COOR^3$;
  $R^3$ is H, —$C_{1-6}$-alkyl, —$C_{3-8}$-cycloalkyl, aryl, het or hetaryl;
  $R^4$ is H, —$C_{1-6}$-alkyl, —$C_{3-8}$-cycloalkyl, —OH, —SH, —$NH_2$, —CN, halogen;
  $R^{LG}$ is H or a suitable leaving group or protecting group;
  D —$C_{5-10}$-alkenylen, —$C_{5-10}$-alkynylen both optionally containing one, two or three heteroatoms selected from O, S, $NR^3$.

and the source of said transition metal complex is a ruthenium catalyst useful for metathesis reactions. More preferred is a process wherein product of the metathesis reaction is a compound of general formula 3a,

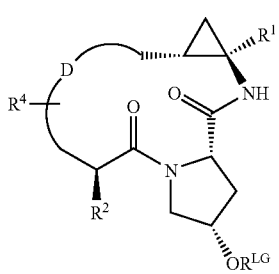

3a wherein $R^1$, $R^2$, $R^3$, $R^4$ and D are defined as above and $R^{LG}$ is a suitable leaving group most preferred is a process, wherein product of the metathesis reaction is a compound of general formula 3b,

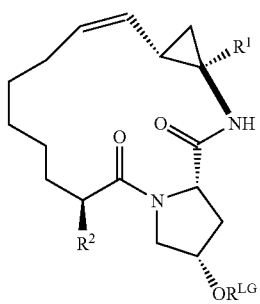

wherein $R^{LG}$ is a suitable leaving group and
$R^1$ is H, —COR³, —COOR³;
$R^2$ is —NH—COR³, —NH—CONHR³, —NH—COOR³;
$R^3$ is H, —$C_{1-6}$-alkyl, —$C_{3-8}$-cycloalkyl.

Another embodiment of the invention is a process for manufacturing a compound of formula 1

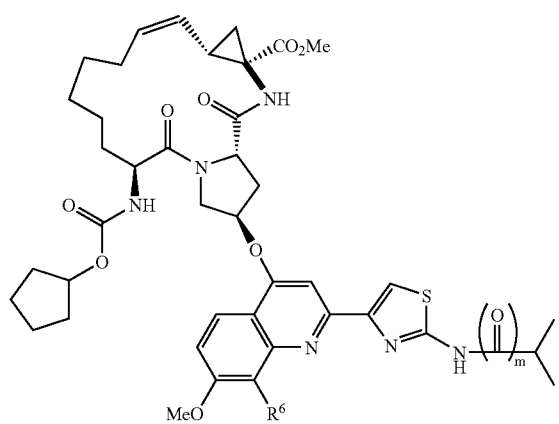

wherein $R^6$ is H or —$CH_3$ and m is 0 or 1. comprising,
I) ring closure metathesis reaction of a compound of formula 2 in presence of a useful ruthenium catalyst;

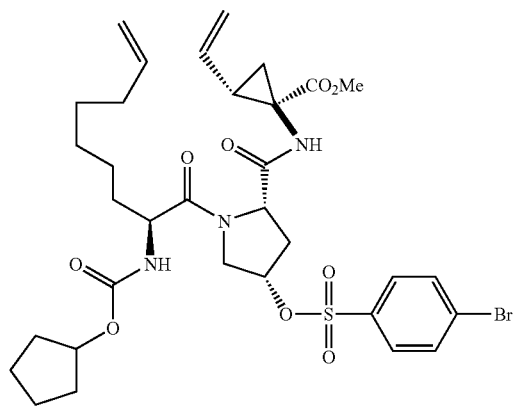

II) diminishing the ruthenium concentration after reaction according to one of the above described procedures;

III) reacting the resulting compound of formula 3c with a compound of formula 4, wherein $R^6$ and m are defined as above;

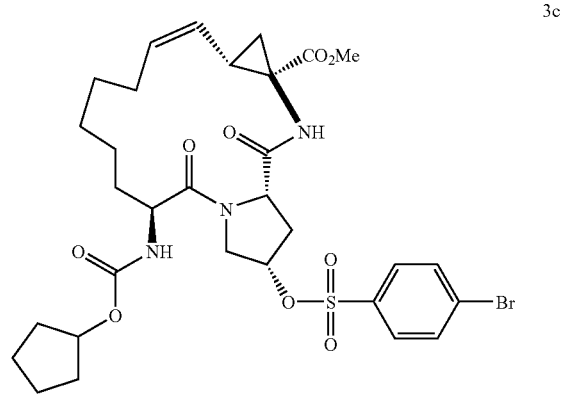

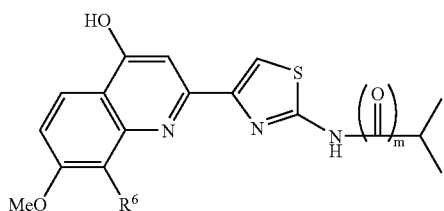

IV) saponification of the resulting compound of formula 5, wherein $R^6$ and m are defined as above;

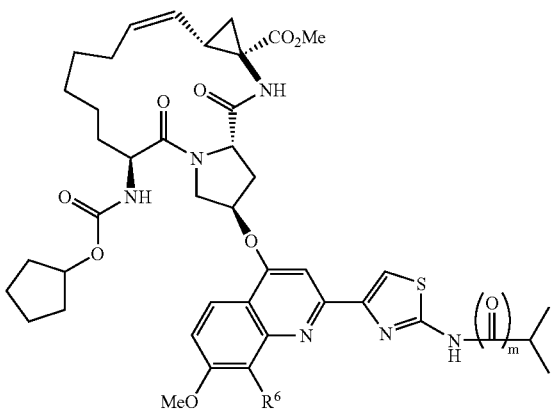

Preferred is a process for manufacturing a compound 3c comprising ring closure metathesis reaction of a compound 2 in presence of a useful ruthenium catalyst;

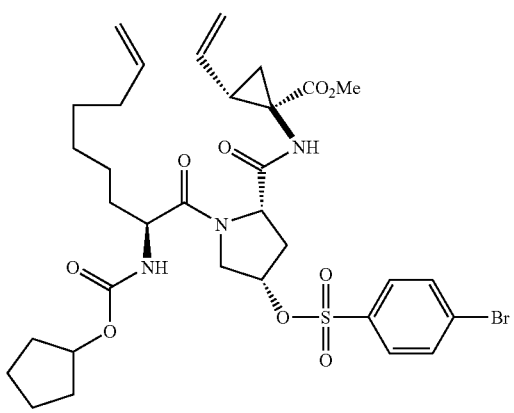

and removing the ruthenium content after reaction according to one of the above described procedures.

This method is particularly effective for the diminishing the concentration of ruthenium complexes, especially of ruthenium complexes containing a metalla-heterocycle, more preferably of ruthenium complexes containing a metalla-heterocycle useful for catalysing metathesis reactions, preferably ring closing metathesis reaction, ring opening metathesis reaction or cross metathesis reaction.

Preferred ruthenium complexes are compounds of formula 6 or 7

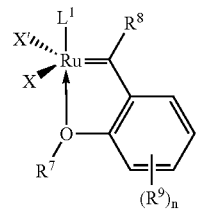

6

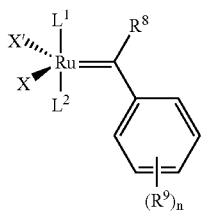

7 wherein

X and X' are anionic ligands, preferably F, Cl, Br, I, most preferably Cl;

$L^1$ is a neutral ligand, preferably $PCy_3$ or

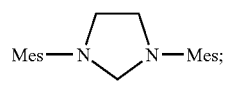

$L^2$ is a neutral ligand, preferably $P(-C_{1-6}\text{-alkyl})_3$, $P(-C_{1-6}\text{-cycloalkyl})_3$ or $PPh_3$, most preferably $PCy_3$ $R^7$ is $-C_{1-6}$-alkyl, $-C_{1-6}$-haloalkyl, $-C_{3-8}$-cycloalkyl or $-C_{7-13}$-aralkyl; preferably $-C_{1-6}$-alkyl, most preferably iso-propyl;

$R^8$ is H, $-C_{1-6}$-alkyl, $-C_{2-6}$-alkenyl, $-C_{2-6}$-alkynyl or phenyl, most preferably H;

$R^9$ is each independently $-C_{1-6}$-alkyl, $-C_{1-6}$-alkoxy, phenyl, F, Cl, $-NO_2$, $-CN$, $-CF_3$, $-OCF_3$, $-CO-R^{10}$, $-SO_2-R^{10}$ or $-PO(R^{10})_2$;

$R^{10}$ is $-C_{1-6}$-alkyl or $-C_{3-8}$-cycloalkyl, both optionally substituted by one or more group selected from each independently F, Cl, Br, I or $-C_{1-6}$-alkoxycarbonyl, or phenyl or heteroaryl both optionally substituted by one or more group selected from each independently F, Cl, Br, I, $-C_{1-6}$-alkyl, $-C_{1-6}$-alkoxy, $-NO_2$, $-CN$, $-CF_3$, $-OCF_3$ or $-C_{1-6}$-alkoxycarbonyl;

n is 0, 1, 2, 3, 4 or 5;

and Cy has the meaning of cyclohexyl, Mes has the meaning of mesityl.

More preferred ruthenium complexes are compounds of formula 6 or 7

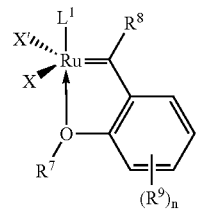

6

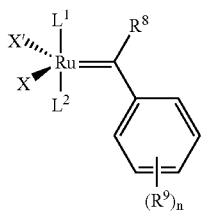

7 wherein

X and X' are anionic ligands, preferably F, Cl, Br, I, most preferably Cl;

$L^1$ is a neutral ligand, preferably $PCy_3$ or

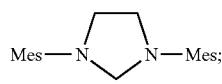

$L^2$ is a neutral ligand, preferably $P(-C_{1-6}\text{-alkyl})_3$, $P(-C_{1-6}\text{-cycloalkyl})_3$ or $PPh_3$, most preferably $PCy_3$ $R^7$ is $-C_{1-6}$-alkyl, $-C_{1-6}$-haloalkyl, $-C_{3-8}$-cycloalkyl or $-C_{7-13}$-aralkyl; preferably $-C_{1-6}$-alkyl, most preferably iso-propyl;

$R^8$ is H, $-C_{1-6}$-alkyl, $-C_{2-6}$-alkenyl, $-C_{2-6}$-alkynyl or phenyl, most preferably H;

$R^9$ is each independently $-C_{1-6}$-alkyl, $-C_{1-6}$-alkoxy, phenyl, F, Cl, $-NO_2$, $-CN$, $-CF_3$, $-OCF_3$ n is 0, 1, 2, 3, 4 or 5;

and Cy has the meaning of cyclohexyl, Mes has the meaning of mesityl.

Most preferred are the ruthenium complexes of formula 6a, 6b and 6c.

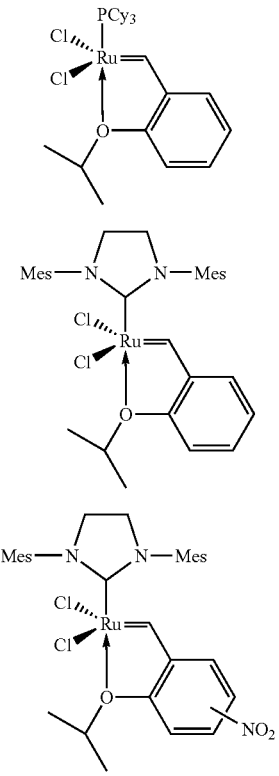

As with prior embodiments, the solubility-enhancing compound may be added to the first solution or the second solution, or the combined solutions. However, it is generally preferred that the solubility-enhancing compound is added to the first solution prior to the combining of the first solution with the second solution.

Although the present invention has been described with examples and references to preferred embodiments, it should be appreciated that the above descriptions were for the purposes of illustration only and not intended in any way to limit the scope of the present invention.

EXPERIMENTAL SECTION

EXAMPLE 1

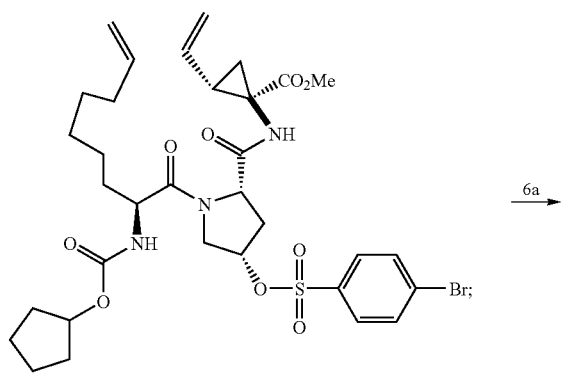

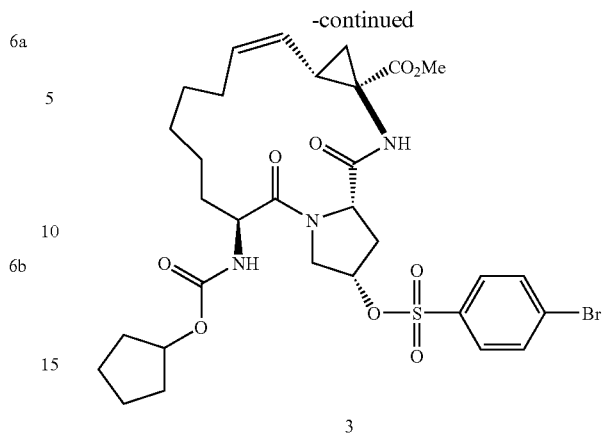

Into a flask, equipped with a mechanical stirrer, a condenser, a nitrogen inlet, a dropping funnel and a heating jacket toluene (2 l) is added at ambient temperature. The solvent is flushed with nitrogen and heated to 80° C., a 36.3% solution of 2 in toluene (55.1 g), is added to the reactor. After 15 minutes a first portion of solid Hoveyda catalysts 6a (0.163 g) is added, and repeated twice (60 and 120 minutes later); so that the total amount of Hoveyda catalyst at the end is 0.489 g.

After HPLC-analysis indicates >97% conversion of starting material the reaction is stopped by cooling the reactor content to ambient temperature. Three metathesis batches according to Example 1 are combined and further used for metal scavenging experiments.

EXAMPLE 2

Into a flask, equipped with a mechanical stirrer, a condenser and a heating jacket the clear metathesis solution from Example 1 is added (500 ml, containing ca. 6.6 mmole of 3). The content is heated to the desired temperature (see table 1) and the appropriate metal scavenger (see table 1), is added and the resulting mixture is stirred for 360 minutes. Thereafter the solution is cooled to ambient temperature and watery extracted, wherein the extraction processes consist of 1N hydrochloric acid (1×70 mL) and water (2×70 mL). The resulting organic phases are used in the further isolation processes.

EXAMPLE 3

The toluene solution of metathesis product 3 after watery extraction according to example 2 (ca. 100 mL) is evaporated to dryness (rotary evaporator). The residue is analyzed for its ruthenium content. The results are summarized in table 1 and 2 under V3 ($B^1$-D).

EXAMPLE 4

The toluene solution of metathesis product 3 after watery extraction according to example 2 (400 ml) is concentrated by distillation to 80 mL. Charcoal powder (1.0 g, Acticarbon LS) is added and the mixture is heated up to 50° C. for 120 minutes, cooled to ambient temperature and the charcoal powder is filtered off. The remaining mixture is further concentrated (22 ml) and added to methyl cyclohexane (114 mL) at 0° C. The resulting precipitate is isolated by filtration, rinsed with cold methyl cyclohexane (2×20 mL), and vacuum dried (20 hours, at 35° C.). The yield of isolated metathesis product 3 (white solid) is 3.4–3.9 g (85–97%). The ruthenium content of the metathesis products are listed in table 1 and 2 under V4.

TABLE 1

Experimental conditions and results for metal scavenging experiments (Mixture 1)

| Exp. | scavenger | m [g] (M) [mmole] | Mol % | T [° C.] | Ru [ppm] V3 | Ru [ppm] V4 |
|---|---|---|---|---|---|---|
| A | none | — | — | 80 | 2250 | — |
| B[1] | imidazole | 1.44 (21.1) | 100 | 80 | 216 | 72 |
| C | benzimidazole | 2.49 (21.1) | 100 | 80 | 472 | 288 |
| D | triazole | 1.46 (21.1) | 100 | 80 | 365 | 246 |

TABLE 2

Experimental conditions and results for metal scavenging experiments (Mixture 2)

| Exp. | scavenger | m [g] (M) [mmole] | Mol % | T [° C.] | Ru [ppm] V3 | Ru [ppm] V4 |
|---|---|---|---|---|---|---|
| B[2] | imidazole | 1.44 (21.1) | 100 | 80 | 149 | 49 |
| B[3] | imidazole | 1.44 (21.1) | 100 | 60 | 271 | 178 |
| B[4] | imidazole | 0.72 (11.5) | 50 | 80 | 267 | 112 |
| B[5] | imidazole | 2.88 (42.2) | 200 | 60 | 249 | 104 |

We claim:

1. A process for diminishing the concentration of a metal complex in a solution containing said complex comprising adding to said solution an optionally fused and/or optionally substituted heterocyclic compound containing at least two nitrogen atoms.

2. A process according to claim 1 for diminishing the concentration of a metal complex in a solution containing said complex comprising adding to said solution an optionally fused and/or optionally substituted het or hetaryl, wherein
het is a four to eight membered, non-aromatic heterocyclic compound containing two, three or four nitrogen atoms and
hetaryl is a five or six membered, aromatic heterocyclic compound containing two or three nitrogen atoms.

3. A process according to claim 1, wherein the metal complex is a transition metal complex.

4. A process according to claim 1, wherein each atom of said heterocyclic compound is optionally substituted by —$C_{1-6}$-alkyl, —$C_{1-6}$-alkyl-OH, —$C_{1-6}$-alkoxy, —$C_{1-6}$-phenyl or phenyl.

5. A process according to claim 1 for diminishing the concentration of a transition metal complex in a first solution containing said complex by the addition of a second solution, comprising the steps:
(a) adding to the first solution a solubility-enhancing compound that enhances the solubility of said complex in the second solution;
(b) combining the first solution with the second solution wherein the second solution is immiscible with the first solution;
(c) mixing the first solution and second solution together; and,
(d) removing the second solution from the first solution; wherein the solubility-enhancing compound is an optionally fused heterocyclic compound containing at least 2 nitrogen atoms, wherein each atom of the ring each independently is optionally substituted by —$C_{1-6}$-alkyl, —$C_{1-6}$-alkyl-OH, —$C_{1-6}$-alkoxy, —$C_{1-6}$-phenyl or phenyl.

6. A process according to claim 5, wherein the solubility-enhancing compound is an optionally fused and/or optionally substituted, five-, six- or seven membered aromatic or non-aromatic heterocyclic compound, containing two or three nitrogen atoms.

7. A process according to the claim 5, wherein the solubility-enhancing compound is imidazole, benzimidazole, pyrazole or triazole.

8. A process according to any of the claim 5, wherein the metal of said metal complex is selected from the group consisting of Cu, Ru, Fe, Ni, Pd, Pt, Rh or W.

9. The process according to any of the claim 5 further comprising after removing the second solution from the first solution:
(e) adding a solid adsorbent to the first solution; and
(f) removing all solid residues from the first solution.

10. A process according to claim 1 for diminishing the concentration of a transition metal complex in a reaction mixture containing said complex and a product of a metathesis reaction, comprising the steps a–d or steps a' to d':
a) adding to the reaction mixture an optionally substituted heterocyclic compound containing at least 2 nitrogen atoms as a solubility-enhancing compound that enhances the solubility of said complex in an aqueous solution, to obtain a first solution;
b) heating the first solution to 40–120° C.;
c) stirring the resulting mixture for 60–600 minutes; and
b) extracting the resulting mixture with an aqueous solution; or
a') heating the reaction mixture to 40–120° C.;
b') adding to the reaction mixture an optionally substituted heterocyclic compound containing at least 2 nitrogen atoms as a solubility-enhancing compound that enhances the solubility of said complex in an aqueous solution, to obtain a mixture;
c') stirring the resulting mixture for 60–600 minutes; and
d') extracting the resulting mixture with an aqueous solution.

11. A process according to claim 10, wherein step a) or step b') comprises adding to the reaction mixture an optionally fused five-, six- or seven membered aromatic or non-aromatic heterocyclic compound, containing two or three nitrogen atoms, wherein each atom of the ring each independently are optionally substituted by —$C_{1-6}$-alkyl, —$C_{1-6}$-alkyl-OH, —$C_{1-6}$-alkoxy, —$C_{1-6}$-phenyl or phenyl as a solubility-enhancing compound that enhances the solubility of said complex in the aqueous solution.

12. A process according to claim 10, wherein step a) or step b') comprises adding a compound selected from the group consisting of imidazole, benzimidazole, pyrazole or triazole as a solubility-enhancing compound that enhances the solubility of said complex in the aqueous solution.

13. A process according to claim 10 wherein the molar ratio of transition metal and solubility-enhancing compound is between 1:10 and 1:600.

14. A process according to claim 10, wherein step d) comprises:
(1) extracting the first solution with 1N hydrochloric acid; and then
(2) extracting the first solution at least twice with water.

15. A process according to claim 10, wherein the remaining concentration of transition metal after steps a–d is less then 1000 ppm.

16. A process according to claim 10, wherein step d) is followed by the steps e–h comprising:
e) adding a solid adsorbent;
f) heating the resulting mixture to 20–100° C.;
g) stirring the resulting mixture for 10–500 minutes; and
h) removing the solid residues.

17. A process according to claim 16, wherein the solid adsorbent is charcoal powder.

18. A process according to claim 16, wherein the remaining concentration of transition metal after steps a–h is less then 500 ppm.

19. A process according to claim 10, wherein the reaction mixture is a crude product solution of a metathesis reaction, said product solution containing a compound of formula 3:

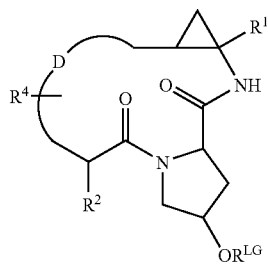

3 wherein
R¹ is H, —COR³, —COOR³, —CO—NHR³, —NH—COR³, —NH—COOR³;
R² is —OR³, —NHR³, —NH—COR³, —NH—CONHR³, —NH—COOR³;
R³ is H, —C$_{1-6}$-alkyl, —C$_{3-8}$-cycloalkyl, aryl, het or hetaryl;
R⁴ is H, —C$_{1-6}$-alkyl, —C$_{3-8}$-cycloalkyl, —OH, —SH, —NH₂, —CN, or halogen;
R$^{LG}$ is H or a suitable leaving group or protecting group;
D —C$_{5-10}$-alkenylene or —C$_{5-10}$-alkynylene, each optionally containing one, two or three heteroatoms selected from O, S, NR³,
and the source of said transition metal complex is a ruthenium catalyst useful for catalyzing the metathesis reaction.

20. A process according to claim 19, wherein the compound of formula 3 is a compound of formula 3a:

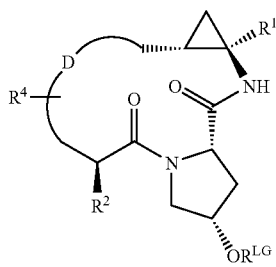

3a wherein R¹, R², R⁴, and D are defined as in claim 19;
R$^{LG}$ is a suitable leaving group.

21. A process according to claim 19, wherein the compound of formula 3 is a compound of formula 3b:

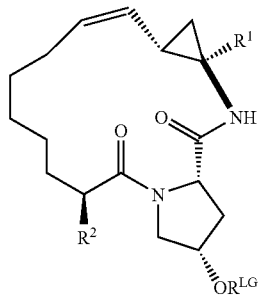

3b wherein
R¹ is H, —COR³, —COOR³;
R² is —NH—COR³, —NH—CONHR³, —NH—COOR³;
R³ is H, —C$_{1-6}$-alkyl, —C$_{3-8}$-cycloalkyl.
R$^{LG}$ is a suitable leaving group.

22. A process according to claim 19, wherein the compound of formula 3 is a compound of formula 3c:

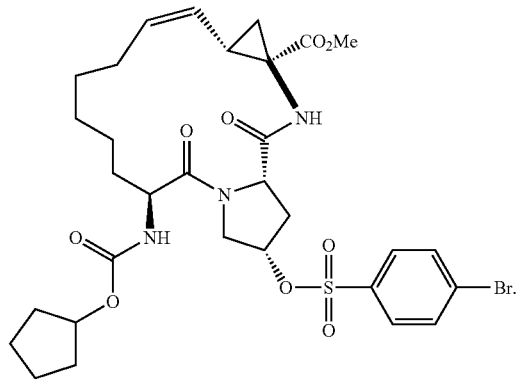

3c

23. A process for manufacturing a compound of formula 1

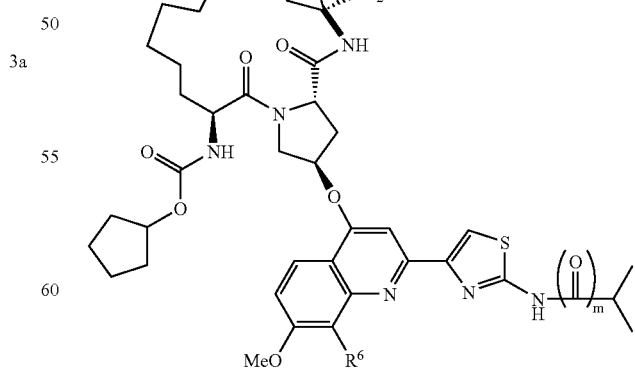

1 wherein R⁶ is H or —CH₃ and m is 0 or 1, comprising:
I) ring-closing a compound of formula 2 in the presence of a ruthenium catalyst:

2

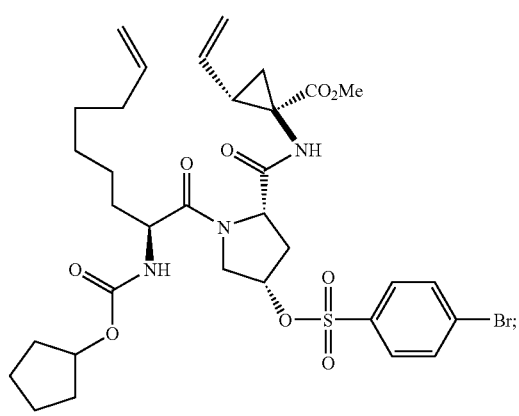

II) diminishing the ruthenium concentration in the resulting reaction mixture obtained in step (I) by using a process according to claim 1;

III) reacting the resulting compound 3c with a compound of formula 4, wherein $R^6$ and m are defined as above:

3c

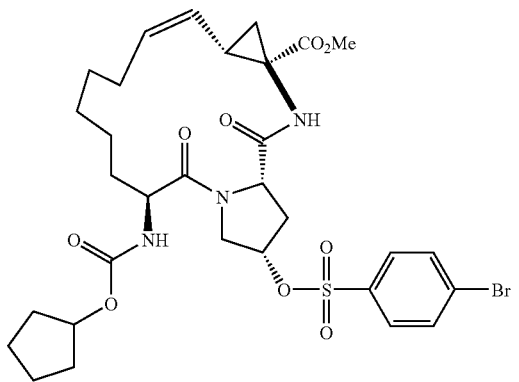

-continued

4

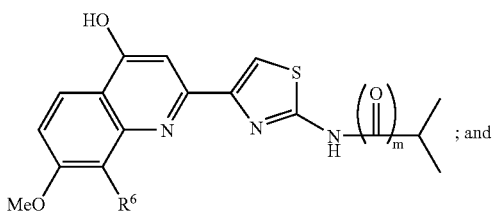
; and

IV) saponifying the resulting compound of formula 5, wherein $R^6$ and m are defined as above, to obtain a compound of formula 1 defined above:

5

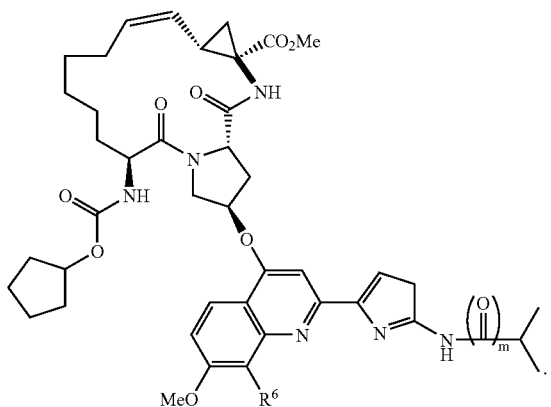

.

* * * * *